Figure 3:
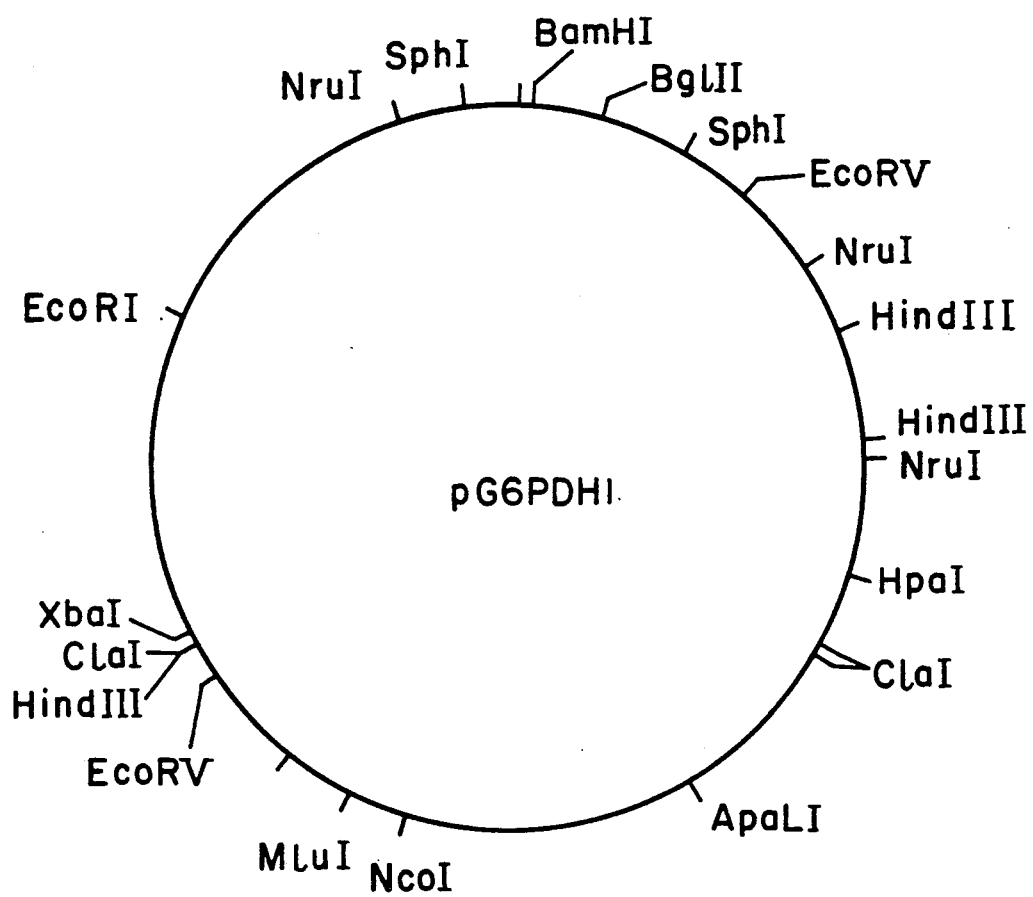

United States Patent [19]

Sagai et al.

[11] Patent Number: 5,137,821
[45] Date of Patent: Aug. 11, 1992

[54] GENE AND PROCESS OF MAKING GLUCOSE-6-PHOSPHATE DEHYDROGENASE

[75] Inventors: Hitoshi Sagai; Kimiko Hattori; Mamoru Takahashi, all of Shizuoka, Japan

[73] Assignee: Toyo Jozo Company, Ltd., Shizuoka, Japan

[21] Appl. No.: 450,588

[22] Filed: Dec. 13, 1989

[30] Foreign Application Priority Data

Dec. 29, 1988 [JP] Japan .................. 63-334629

[51] Int. Cl.$^5$ ............... C12N 9/04; C12N 15/53; C12N 15/70; C12N 1/21
[52] U.S. Cl. ............................ 435/190; 536/27; 435/320.1; 435/252.33; 435/69.1; 435/252.3
[58] Field of Search ............... 536/27; 435/69.1, 320.1, 435/252.33, 190, 252.3, 172.3; 935/14

[56] References Cited

U.S. PATENT DOCUMENTS 4,331,762  5/1982  Nakajima et al. .

FOREIGN PATENT DOCUMENTS 029976  6/1981  European Pat. Off. .
3041744  5/1981  Fed. Rep. of Germany .
63-43079  8/1988  Japan .

OTHER PUBLICATIONS

Lauwers, A. M. et al. 1981. *Arch. Microbiol.* vol. 130, pp. 159–164.
Bergey's Manual of Systematic Bacteriology 1986, Ed. P.H.A. Sheath et al. Williams & Wilkins, Baltimore, vol. 2 pp. 1122–1123.
Opheim, D. et al. 1973. *J. Bacteriol.* vol. 116 pp. 1150–1159.
Okuno, H. et al. 1986. *Biological Abstracts* vol. 81 No. 3, Abs. 27058.
Lampel, K. A. et al. 1986. *J. Bacteriol* vol. 166 pp. 238–243.
Young, R. A. et al. 1983. *Proc. Nat Acad Sci USA* vol. 80 pp. 1194–1198.
Persico et al., Nature 294: 778–780, 1981.
Haberstich et al, Arch. Microbiol. 98:275–287, 1974.
Takizawa et al., Proc. Natl. Acad. Sci. USA 83:4157–4161, 1986.
Ho et al., Nucleic Acids Res. 16(15):7746, 1988.
Enzyme Handbook (Asakura Press, 1984) pp. 20–21.
Okuno et al., J. Applied Biochem. 7: 192–201, 1985.

*Primary Examiner*—Richard A. Schwartz
*Assistant Examiner*—Mary E. Mosher
*Attorney, Agent, or Firm*—Darby & Darby

[57] ABSTRACT

Glucose-6-phosphate dehydrogenase which is an enzyme for assaying creatinekinase for diagnolyzation of myocardial infraction is produced by culturing a transformant having DNA which codes amino acid sequence shown from its N-terminal in FIG. 1 and which is extraneous to a host to have genetic information of the DNA expressed and collecting glucose-6-phosphate dehydrogenase from the culture.

9 Claims, 8 Drawing Sheets

FIG. 1A

```
  1                     5                         10                      15
ThrAspValGlnProLysAlaThrIleValIleProGlyAlaThrGly
                       20                        25                       30
AspLeuAlaLysArgLysLeuPheProSerIleTyrLysLeuTyrGln
                       35                        40                       45
LysGlyLysLeuAlaGluGlnPheAlaValValGlyValAlaArgArg
                       50                        55                       60
ProHisThrAspGluSerPheArgSerTyrValArgGluThrIleGlu
                       65                        70                       75                    80
GluAlaThrLysGlnGluLeuIleAspAspLysPheIleSerHisPhe
                       85                        90                       95
TyrTyrHisSerLeuAspAlaThrAsnThrGlnSerTyrGluGlnLeu
                      100                       105                      110
AsnGluLeuLeuThrArgValGluGlnPheHisIleProGlyAsn
                      115                       120                      125
ArgIlePheTyrLeuAlaMetAlaProGluPhePheGlyThrIleThr
```

FIG. 1B

```
          130                    135                    140
SerHisLeuLysSerGluGlyLeuThrAlaThrAsnGlyTrpThrArg
  145                    150                    155                    160
LeuValIleGluLysProPheGlyHisAspLeuGlnSerAlaLysLys
              165                    170                    175
LeuAsnGluGluIleArgGlnSerPheSerGluGluGlnIlePheArg
      180                    185                    190
IleAspHisTyrLeuGlyLysLysGluMetValGlnAsnIleGluValIle
    195                    200                    205
ArgPheAlaAsnAlaIlePheGluProLeuTrpAsnAsnArgPheIle
          210                    215                    220
AlaAsnIleGlnIleIleThrSerSerGluThrLeuGlyValGluAspArg
        225                    230                    235                    240
GlyArgTyrTyrAspHisSerGlyAlaLeuArgAspMetValGlnAsn
                  245                    250                    255
HisMetLeuGlnMetValAlaLeuLeuAlaMetGluProProIleLys
```

FIG. IC 260 265 270
LeuThrThrAspIleArgSerGluLysValLysValLeuArgAla 275 280 285
LeuArgProMetThrHisAspAspValGluThrTyrPheValArgGly 290 295 300
GlnTyrGlyArgGlyIleValArgGlyGlnGlnValValGlyTyrArg 305 310 315 320
GluGluHisAsnValAspProAsnSerAsnThrGluThrPheValAla 325 330 335
GlyLysLeuMetIleAspAsnPheArgTrpAlaGlyValProPheTyr 340 345 350
IleArgThrGlyLysArgMetThrGluLysSerThrLysIleValVal 355 360 365
GlnPheLysAspValProMetAsnLeuTyrTyrArgThrSerGluHis 370 375 380
ValHisProAsnLeuLeuValIleHisIleGlnProAspGluGlyIle

FIG. 1D 385 390 395 400
ThrLeuHisLeuAsnAlaAlaLysLysSerGlyGluAsnMetLysThrThr 405 410 415
AlaIleLysLeuAspTyrCysAsnAsnCysIleAspGlyIleAsnThr 420 425 430
ProGluAlaTyrGluLysLeuLeuLeuTyrAspCysMetArgGlyAspAla 435 440 445
ThrAsnPheThrHisTrpAspGluValAlaAlaAlaSerTrpSerPheVal 450 455 460
AspProIleSerGluValTrpAlaAsnThrLysAlaValAspPhePro 465 470 475 480
AsnTyrGluAlaGlySerMetGlyProLysAlaAspGluLeuLeu 485 490
GlnLysAspGlyPheHisTrpTrpProLeuAsnGlyThrIle

FIG. 2A

```
ACTGACGTAC AACCAAAAGC GACAATTGTA ATTTTGGTG  CGACTGGCGA  CTTAGCAAAA   60
CGTAAACTAT TCCCATCTAT TTATAAACTT TATCAAAAAG GAAAGCTTGC TGAACAGTTT  120
GCGGTTGTTG GTGTTGCCCG TCGTCCACAT ACTGACGAGT CATTTCGTTC CTATGTAAGA  180
GAAACGATTG AGGAAGCAAC GAAACAAGAA CTGATTGATG ACAAATTTAT TTCTCATTTT  240
TACTATCATT CATTAGATGC AACAAATACG CAATCATATG AACAATTAAA TGAATTATTA  300
ACTCGTGTGG AAGAACAATT TCATATTCCA GGCAACCGCA TTTTTTACTT GGCGATGGCA  360
CCGGAATTTT TCGGAACGAT TACATCGCAC TTGAAATCCG AGGGGCTGAC GGCCACAAAC  420
GGATGGACGC GATTAGTCAT TGAAAAACCG TTCGGTCATG ATTTACAAAG CGCAAAAAAA  480
```

FIG. 2B

```
CTAAATGAAG  AAATACGCCA  ATCGTTTTCA  GAGGAGCAAA  TTTTCCGTAT  TGACCATTAT  540
CTCGGCAAAG  AAATGGTGCA  AAACATCGAG  GTCATTCGCT  TTGCGAACGC  CATTTTCGAA  600
CCGCTCTGGA  ATAACCGCTT  TATTGCCAAT  ATTCAAATTA  CATCAAGCGA  AACGCTCGGT  660
GTAGAAGATC  GCGGCCGCTA  TTATGACCAT  TCCGGCGCGC  TTCGCGATAT  GGTACAAAAC  720
CATATGTTGC  AAATGGTTGC  CCTTTTGGCG  ATGGAGCCTC  CGATTAAGCT  GACAACTGAT  780
GATATTCGTA  GCGAAAAAGT  AAAAGTGCTT  CGTGCGCTTC  GTCCGATGAC  GCACGATGAC  840
GTAGAAACAT  ATTTCGTGCG  TGGACAATAC  GGGCGTGGCA  TCGTGCGCGG  ACAACAAGTC  900
GTCGGATATC  GTGAAGAACA  TAATGTCGAT  CCAAACTCCA  ATACGGAAAC  ATTTGTTGCA  960
```

FIG. 2C

```
GGGAAACTAA TGATCGACAA CTTCCGCTGG GCAGGTGTGC CGTTTTACAT ACGAACAGGA 1020
AAACGAATGA CAGAAAAATC AACAAAAATT GTTGTGCAAT TTAAAGATGT GCCGATGAAT 1080
TTATATTATC GCACAAGCGA GCACGTTCAT CCGAATTTGC TCGTCATCCA CATTCAGCCC 1140
GATGAAGGCA TTACCCTTCA TTTAAACGCG AAAAAAAGCG GCGAAAACAT GAAAACGACA 1200
GCAATTAAGC TCGATTACTG CAACAACTGC ATCGACGGCA TTAATACGCC GGAAGCGTAT 1260
GAGAAATTGT TATATGACTG CATGCGCGGC GATGCGACAA ACTTTACACA CTGGGACGAA 1320
GTCGCTGCTT CTTGGAGCTT TGTCGACCCA ATTTCTGAAG TATGGGCAAA TACGAAAGCG 1380
GTGGACTTCC CGAACTACGA AGCTGGATCG ATGGGGCCGA AAAAAGCGGA TGAACTATTG 1440
CAAAAAGACG GCTTCCACTG GTGGCCATTA AATGGAACAA TA                     1500
```

GENE AND PROCESS OF MAKING GLUCOSE-6-PHOSPHATE DEHYDROGENASE

The present invention relates to a novel gene of glucose-6-phosphate dehydrogenase and a process to produce glucose-6-phosphate dehydrogenase using the gene.

Glucose-6-phosphate dehydrogenase, which may be abbreviated as G6PDH hereinafter, is an enzyme which catalyzes an enzymatic reaction to produce gluconolactone-6-phosphate and the reduced form of NAD(P), i.e. NAD(P)H, from glucose-6-phosphate and NAD or NADP which is referred to as NAD(P) hereinafter. The enzyme is widely distributed in animal and plant kingdoms, and its high activity is observed in adrenal cortex, spleen and mammary gland during breast feeding among other animal tissues. As such enzyme reported to be purified, the following is known; G6PDH derived from mammary gland [J. Biol. Chem. 236, 754–758 (1961)]; G6PDH derived from liver [Biochem. J. 55, 400–408 (1953)]; G6PDH from red blood cell [J. Biol. Chem. 224, 1047–1064 (1957), Meth. Enzymol., 9, 126–131 (1966) and J. Biol. Chem. 241, 4966–4976 (1966)]; G6PDH from beer yeast [J. Biol. Chem 216, 67–79 (1955)]; G6PDH from *Candida utilis* [Z. physiol. Chem., 350, 626–634 (1969), and Biochim. Biophys. Acta, 191, 509–516 (1969)]; G6PDH from *Leuconostoc mesenteroides, Azotobacter vinelandii* and *Pseudomonas fluorescens* [Meth. Enzymol. 1, 328–334 (1955)](Enzyme Handbook, pages 20–21, Asakura Press, 1984, a third revised edition of the first press). G6PDH derived from some bacterium belonging to the genus *Bacillus* is also known as described in Arch. Microbiol., 98, 275–287 (1974) and Japanese Patent Publication No. 43079/1988. Also, the nucleotide sequence of human G6PDH gene and that of rat G6PDH gene are reported in Proc. Natl. Acad. Sci., USA, 83, 4157–4161 (1986) and Nucleic Acids Research 16, 7746 (1988).

G6PDH currently used as an enzyme for the assay of creatinekinase in order to diagnose myocardial infarction is an extremely useful enzyme. G6PDH when used as a diagnostic reagent is required to have long-term stability as well as thermal stability. There are problems in conventional production of G6PDH by using G6PDH-producing bacteria. That is, the G6PDH productivity of these G6PDH-producing bacteria is so low that it is difficult to supply a large amount of the enzyme at low cost and removal of contaminating enzymes, for example, NAD(P)H oxidase and lactate dehydrogenase, is difficult.

The present inventors conducted intensive research in order to solve the above problems to succeed in isolating and purifying, from the bacterium defined below belonging to the genus *Bacillus*, a gene coding the amino acid sequence of the polypeptide constituting G6PDH and determining specifically the primary structure of the DNA and that of the amino acid sequence constituting of said enzyme. The inventors confirmed that the nucleotide sequence of the DNA and the amino acid sequence in accordance with the present invention are novel substances because they are different in their constitution and homology from the nucleotide sequences of the genes of the human G6PDH and rat G6PDH and the amino acid sequences thereof aforementioned.

In the accompanying Drawings,

FIG. 1A–D shows the amino acid sequence of the polypeptide constituting G6PDH.

FIG. 2A–C shows DNA sequence coding the amino acid sequence of the poplypeptide constituting G6PDH.

FIG. 3 shows a cleavage map of the plasmid pG6PDH1 by restriction enzymes.

The present invention provides

DNA coding the amino acid sequence shown from its N-terminal in FIG. 1;

a plasmid characterized by having DNA coding the amino acid sequence shown from its N-terminal in FIG. 1;

a transformant characterized by carrying a plasmid having DNA which codes the amino acid sequence shown from its N-terminal in FIG. 1 and which is foreign to a host;

a process for preparing glucose-6-phosphate dehydrogenase, comprising culturing a transformant carrying a plasmid having DNA which codes the amino acid sequence shown from its N-terminal in FIG. 1 and which is foreign to a host in order to express the genetic information of the DNA and collecting glucose-6-phosphate dehydrogenase from the culture; and a polypeptide composed of the amino acid sequence shown from its N-terminal in FIG. 1.

According to the present invention, the amino acid sequence shown in FIG. 1 may contain amino acid residues or polypeptide residues at N-terminal and C-terminal, and it may also contain one or plural amino acid residues upstream. Thr at N-terminal, the amino acid residue(s) being Met or a signal peptide; it may also contain one or more amino acid residues downstream Ile at C-terminal.

The novel DNA coding the amino acid sequence shown in FIG. 1 may be DNA comprising a series of any one of codons corresponding to each amino acid constituting the amino acid sequence including the amino acid residues or the polypeptide residues at N-terminal and C-terminal.

Such DNA is represented by DNA having the nucleotide sequence shown from its 5'-terminal in FIG. 2. The DNA may be a DNA having one or more codons coding amino acids upstream the 5'-terminal, provided that the codons are other than TAA, TAG and TGA. Preferably, the DNA may have a codon ATG or an initiation codon except ATG, or codons corresponding to a signal peptide. Downstream ATA at the 3'-terminal, the DNA may have one or more codons coding amino acids or a translation terminating codon; furthermore, in case that the DNA has one or more codons coding amino acids at the 3'-terminal, the DNA may preferably have a translation terminating codon at 3'-terminal of the codon coding the amino acid.

DNA coding the amino acid sequence shown in FIG. 1 or DNA shown in FIG. 2 may be obtained in the following manner: the DNA, isolated and purified from the G6PDH-producing bacterium as a donor of the G6PDH gene, is cleaved with ultrasonication or restriction enzymes and subsequently linkaged and cyclized at its both blunt ends or cohesive ends by DNA ligase with a plasmid, preferably an expression vector linearized by cleavage. After the resultant recombinant plasmid is transfected into a host bacterium capable of replicating the DNA, the bacterium, having the recombinant plasmid which is obtained through screening using a marker of the vector and the G6PDH activity as indicators, is cultured. DNA as the G6PDH gene may be recovered from the recombinant plasmid isolated and purified from the bacterial culture.

As the bacterium for a donor of the DNA, it is preferable to use *Bacillus* sp.HT-3 having the following taxonomical properties deposited as FERM BP-2172 at the Agency of Industrial Science and Technology, the Fermentation Research Institute.

The *Bacillus* sp. HT-3 strain described above has the following taxonomical properties:

I. Characteristic feature of growth

1. Normal agar slant medium

Shows good growth in filiform. Develops color, ocher or greyish white. It does not produce any soluble dye.

2. Normal agar plate

Forms circular colonies and their circumference is entirely in convex form. The color is ocher or greyish white. It does not produce soluble dye.

3. BCP milk medium

No change observable.

4. Liquid medium (peptone-water)

Shows good growth with uniform turbidity

II. Morphological feature

Bacillus with its circumferential region being round or a little bit curved exists singly or two in chain, or occasionally exists in short-chain form, where tadpole-like cells and spheroidal cells are simultaneously present. Rod cell: 0.5 to 0.8 $\mu m \times 2.0$ to 3.0 $\mu m$ in size; a coccobacillus cell, 1.4 $\mu m$ in size; in addition, endogenous spores are formed at the circumference or sub-circumference of a rod cell but the spores do not inflate the cell; the species are pertrichous and movable.

III. Physiological, biochemical characteristics

| | |
|---|---|
| Gram's stain; | + |
| KOH reaction; | − |
| Capsule formation; | − |
| Acid-fast stain; | − |
| OF test; | 0 (oxidized) |
| Growth under anaerobic condition; | − |
| Growth under aerobic condition; | + |
| Growth temperature | |
| 52° C.; | + |
| 45° C.; | + |
| 37° C.; | − |
| Growth pH | |
| 9.0; | − |
| 8.0; | + |
| 5.2; | + |
| 4.7; | − |
| Salt resistivity | |
| 0% | + |
| 10% | + |
| Catalase production; | + |
| Oxidase production; | + |
| Urease production (SSR); | − |
| Urease production (Chris); | (+) |
| Indole production; | − |
| Hydrogen sulfide (Lead acetate paper); | − |
| Acetoin production; | − |
| MR test; | − |
| Nitrate reduction; | + |
| Denitrification reaction; | − |
| Gelatin decomposition; | − |
| Carbohydrate decomposition; | + |
| Casein decomposition; | (+) |
| Esculin decomposition; | + |
| Cellulose decomposition; | − |
| Tyrsine decomposition; | (+) |
| Efficacy test (Shimmons medium) | |
| Citrates; | − |
| Maleates; | − |
| Malates; | − |
| Gluconates; | − |
| Propionates; | − |
| Malonates; | − |
| Succinates; | − |
| Efficacy test (Christensen medium) | |
| Citrates; | − |
| Maleates; | − |
| Malates; | − |
| Gluconates; | − |
| Propionates; | − |
| Malonates; | − |
| Succinates; | − |
| Gas production from glucose; | − |
| Acid production from sugar ($NH_4H_2PO_4$ used as N source) | |
| Adonitol; | − |
| L(+)-Arabinose; | + |
| Cellobiose; | + |
| Durcitol; | − |
| Mesoerythritol; | − |
| Fructose; | + |
| Galactose; | + |
| Glucose; | + |
| Glycerin; | + |
| Inositol; | + |
| Inulin; | − |
| Lactose; | − |
| Maltose; | + |
| Mannitol; | + |
| Mannose; | + |
| Melezitose; | + |
| Melibiose; | + |
| Raffinose; | + |
| L(+)-Rhamnose; | − |
| D-Ribose; | + |
| Salicin; | + |
| L-Sorbose; | − |
| Sorbitol; | − |
| Carbohydrate: | + |
| Saccharose; | + |
| Treharose; | + |
| Xylose; | + |

(+ positive; (+) weekly positive; − negative)

IV. Principal properties of the present bacterial strain

The present bacterial strain is gram-positive bacillus with round circumference, exists singly or in short-chain; the strain is classified into spore-forming bacteria possessing catalase-production potential. The strain decomposes glucose oxidatively to produce acids.

V. Identification of the present bacterial strain

The present bacterial strain is identified to belong to the genus *Bacillus* according to the principal properties, i.e., gram positive, catalase-production and spore-formation and designated as *Bacillus* sp. HT-3 strain which has been deposited at the Agency of Industrial Science and Technology, the Fermentation Research Institute as FERM BP-2772.

DNA is obtained from a bacterium as a donor of gene as follows. For example, any one of the species of bacteria as donors described above may be cultured with agitation in a liquid medium under aerated condition for about 1 to 3 days and the resultant culture medium is centrifugated to harvest the bacteria followed by lysis to prepare a lysate containing the G6PDH gene. Some treatment with cell-wall solubilizing enzymes such as lysozyme and β-glucanase are conducted for the lysis of the bacteria and if necessary, enzymes such as protease, etc. and surfactants such as sodium laurylsulfate may be also used in combination; furthermore, freezing-thawing as shown in GB 2196018 or a French press treatment as a physical disruption method of cell wall in combination with the aforementioned solubilizing method, may be also used.

In order to isolate and purify DNA from the lysate obtained in this manner, the lysate is subjected to an appropriate combination of the following methods, for example, a deproteinization treatment with phenol extraction, a protease treatment, a ribonuclease treatment, alcohol precipitation, centrifugation and the like, according to the routine methods.

The cleavage method of the bacterial DNA isolated and purified includes ultrasonication and enzyme treatment, preferably a restriction enzyme, more specifically, the Type-II restriction enzyme such as EcoRI, HindIII and BamHI, which affects the specific nucleotide sequences so that the resultant DNA fragment can be easily joined with a vector.

As for the vectors, those were constructed from phages or plasmids capable of autonomously proliferation for genetic recombination are preferable.

As for the phage vectors, $\lambda_{gt}.\lambda C$ and $\lambda_{gt}.\lambda B$ may be used in case of *Escherichia coli* as a host bacterium.

As for the plasmid vectors, pBR322, pBR325, pACYC184, pUC12, pUC13, pUC18, pUC19 and the like may be used in case of *Escherichia coli* as a host bacterium, while pUB110, pC194 and the like may be used in case of *Bacillus subtilis* as a host bacterium. In addition, there may be used a shuttle vector which can autonomously replicate in 2 or more kinds of host-bacteria, such as *Escherichia coli* and *Sacchromyces cerevisiae*. Such vectors may be preferably digested with the same restriction enzymes as are used for cleavage of the bacterial DNA as the donor of the G6PDH gene, to obtain vector fragments.

To join bacterial DNA fragments with vector fragments a known method such as the method using a DNA ligase may be conducted; for example, after annealing of the cohesive ends of the bacterial DNA fragments to those of the vector fragments, a suitable DNA ligase acts to produce a recombinant DNA composed of the bacterial DNA fragments and the vector fragments. If necessary, the DNA and the vector fragments, after annealing, are subsequently transfected into a host bacterium to produce recombinant DNA using a DNA ligase present in the living organisms.

Any host bacterium may be used, in which the recombinant DNA can grow stably and autonomously and the properties of the foreign DNA can be expressed; for example, *Escherichia coli* DH1, *Escherichia coli* HB101, *Escherichia coli* W3110, *Escherichia coli* C600 and the like may be utilized among the species of the host-bacteria belonging to *Escherichia coli*.

The methods for introduction of the recombinant DNA into a host-bacterium may include a method using calcium ion in case of the bacterium belonging to the genus *Escherichia*, whereas in case of the bacterium belonging to the genus *Bacillus*, there may be used the competent cell method and the electrical fusion-transfer method for introduction of a liposomal recombinant DNA into a protoplast host cell. Furthermore, the micro-injection method may be also selected.

Whether introduction of the objective recombinant DNA into a host-bacterium has taken place and may be determined, using a marker for the vector having the objective recombinant DNA such as a drug-resistant marker and a bacterium capable of expressing G6PDH, for example, a bacterium which grow in a selective medium for the drug-resistant marker and which produces G6PDH may be selected preferably by using dyes.

The quantitative relationship generally used in the above genetic manipulation is exemplified as follows: a restriction enzyme of about 1 to 10 U, a ligase of about 300 U and other enzymes of about 1 to 10 U are used for 0.1 to 10 $\mu$g each of the DNA from the donor bacterium and plasmid DNA.

The bacterium obtained thus as a transformant, for example, the bacterium belonging to *Escherichia coli*, more broadly, to the genus *Escherichia*, is able to produce a great amount of G6PDH stably by being cultured in a nutrient medium. For a specific example of the transformant, the DNA shown in FIG. 2 is inserted into the plasmid pACYC184 [see J. Bacteriol, 134, 1141(1981)], transformed the host bacterium *Escherichia coli* DH1 [see T. Maniatis., et al., Molecular Cloning, Cold Spring Harbor (1982), 504–506]and then, the selected bacterium capable of producing G6PDH is defined as *Escherichia coli* DH1.pG6PDH1 deposited as FERM BP-2174 at the Agency of Industrial Science and Technology, the Fermentation Research Institute.

The recombinant DNA, once selected in this manner, can be readily isolated from the transformant having the recombinant DNA and then, it can be introduced into other host bacteria. Furthermore, the recombinant DNA is cleaved with restriction enzymes so as to take out the DNA coding the amino acid sequence of the polypeptide constituting of G6PDH, followed by ligation with the end of the linearized vector obtained by the digestion by the same manner as those described above, to prepare a recombinant DNA possessing a new feature. The new recombinant DNA may be also readily introduced into other host bacteria.

The recombinant DNA and the vector containing the recombinant DNA may be selected by colony-hybridization, using a probe prepared on a partial nucleotide sequence of the DNA coding the amino acid sequence shown in FIG. 1 or the DNA shown in FIG. 2.

G6PDH in accordance with the present invention can be made variant of its peptide using known genetic manipulation techniques and the resulting mutein-coding DNA means an artificial variant gene generated from G6PDH gene of the present invention by the genetic engineering technique; the artificial variant gene can be obtained by using a variety of genetic engineering techniques such as the site-specific base conversion method and the replacement of a specific DNA fragment of the objective gene for an artificial variant fragment. Among some artificial variant genes thus obtained, a mutated DNA of G6PDH provided with particularly excellent features is finally inserted into a vector to create a recombinant DNA and then, the introduction of the resultant recombinant DNA enables to produce G6PDH mutein. Specific examples of vectors which contain G6PDH-coding DNA may include a plasmid (designated as pG6PDH1) derived from *Escherichia coli* DH1. G6PDH. The cleavage map of the plasmid pG6PDH is as shown in FIG. 3.

The nucleotide sequence of DNA encoding the amino acid sequence of the polypeptide constituting of G6PDH thus obtained by the above methods, was determined by the dideoxy method disclosed in Science, 214, 1205–1210 (1981), while the amino acid sequence of the polypeptide constituting of G6PDH was estimated and determined from the nucleotide sequence. Alternatively, the amino acid sequence at its N-terminal of the polypeptide of the G6PDH which was cultured and purified by the method described hereinafter, was determined by a liquid-phase protein sequencer (BECKMAN System 890ME manufactured by Beckmann, Co., Ltd.). Subsequently it was confirmed that the amino acid sequence at least at N-terminal of the G6PDH corresponded to the partial amino acid sequence determined on estimation.

The process for preparing the G6PDH from transformant comprises culturing the transformant in a culture medium to produce the G6PDH in a bacterium or in a culture broth, collecting the bacterium by such means as filtration or centrifugation of the culture broth after completion of the culture, subsequent disrupting the bacterium mechanically or enzymatically such as the use of lysozyme, while EDTA and/or an appropriate surfactant are added, if needed, and isolating and collecting the G6PDH in buffer solution. The resultant G6PDH solution may be concentrated, alternatively, treated with ammonium sulfate fractionation, gel filtration, absorption chromatography including affinity chromatography and ion-exchange chromatography, to yield the G6PDH with high purity.

In case of selecting a suitable host bacterium such as *Escherichia coli*, in particular, a process of heating may be added to the above process preferably. For example, a treatment of the culture broth and the disrupted, solubilized bacterium at 60° C. for 16 hours realizes an extremely simplified purification of G6PDH and furthermore efficient removal of possibly contaminating enzymes which may cause problems in use of the G6PDH for clinical diagnosis. G6PDH having a very good feature with no detectable effect of contaminating enzymes is obtained. The contaminating enzymes may include NAD(P)H oxidase, lactate dehydrogenase, glucose dehydrogenase, glucose isomerase, ATPase, alkaline phosphatase, phosphoglucomutase, hexose-6-phosphate isomerase, NAD(P) nucleosidase, malate dehydrogenase, succinate dehydrogenase and the like. As for NAD(P) H oxidase and lactate dehydrogenase which are difficult to remove and which cause problems in use of G6PDH for clinical diagnosis, the present invention provide G6PDH wherein the activity each of NAD(P) H oxidase and lactate dehydrogenase is 0.0001 unit or less in 100 unit of G6PDH.

The culture condition of the bacterium as transformant may be selected in terms of its physiological requirements for nutrients. Liquid culture may usually be conducted in many cases. Deep aeration culturing with agitation is preferable. As for nutrients, those routinely used for bacterial culture may be widely used. As for carbon sources, any carbohydrates which can be metabolized may be used, for example, glucose, saccharose, lactose, maltose, fructose, honey and the like; as for nitrogen sources, any nitrogen compounds possible for use may be used, for example, peptone, meat broth, yeast extract, casein hydrolyzate and the like. In addition, salts such as phosphates, carbonates, sulfates, salts of magnesium, calcium, potassium, iron, manganese, zinc, etc., specific amino acids and specific vitamins may be used if necessary.

The culturing temperature may be appropriately modified within the range where the bacterium may grow to produce G6PDH, preferably about 20° C. to 42° C. in case of *Escherichia coli*. The culturing period varies more or less depending on culturing conditions; but usually it is about 12 to 48 hours when the culturing is terminated at an appropriate time estimated to reach the maximum yield of G6PDH. Culture medium pH may be also adequately modified within the range wherein the bacterium may grow to produce G6PDH, preferably within the range of 6.0 to 8.0.

The culture broth containing the bacterium as it is is taken to utilize G6PDH present in the culture broth. When the culture broth contains G6PDH, it is separated into the G6PDH-containing solution and the bacterial cells by filtration and centrifugation. When G6PDH is contained in the cells, the bacterium is isolated from the resultant culture broth by, for example, filtration or centrifugation and then disrupted mechanically or enzymatically using lysozyme; if necessary, a chelating agent such as EDTA and/or surfactants are added to solubilize G6PDH to isolate and collect G6PDH in a buffer solution.

The G6PDH-containing solution thus obtained is allowed to precipitate with concentration under reduced pressure, membrane concentration, salting out process using ammonium sulfate or sodium sulfate, or fractional precipitation method using hydrophilic organic solvents, for example, methanol, ethanol and acetone. The precipitate is subsequently dissolved in water and dialyzed against a semipermeable membrane to remove impurities with lower molecular weight. The G6PDH-containing solution purified through gel filtration using adsorbing agents or gel filtration agents, adsorption chromatography such as affinity chromatography, ion-exchange chromatography, etc. is further applied to concentration under reduced pressure and lyophilization until G6PDH in purified form is obtained.

G6PDH having, for instance, the following properties is one of G6PDHs obtained in the manner heretoforementioned.

(1) Activity assay

① Assay of G6PDH activity

| Reaction solution | | |
|---|---|---|
| 0.2M | Phosphate buffer (pH 7.5) | 0.2 ml |
| 10% | BSA (bovine serum albumin) | 0.05 ml |
| 1% | Triton X-100 | 0.1 ml |
| 10 mM | NADP | 0.1 ml |
| 100 U/ml | Diaphorase | 0.05 ml |
| 0.25% | NBT | 0.1 ml |
| 0.1M | Glucose-6-phosphate | 0.2 ml |
| | Distilled water | 0.2 ml |

Procedure

The reaction solution (1.0 ml) of the above composition is taken in a test tube and preliminary heated at 37° C. for 3 minutes, followed by addition of 20 μl of an enzyme solution containing G6PDH. The mixture is left to stand at 37° C. for 10 minutes to react. The reaction is terminated by addition of 2.0 ml of 0.1 N HCl and measured the absorbance at 550 nm. The activity of G6PDH which oxidize 1 μmol of glucose-6-phosphate into gluconolactone-6-phosphate per minute is defined as 1 unit (U).

(2) Assay of NAD(P)H oxidase activity

| Reaction solution | | |
|---|---|---|
| 80 mM | Tris-HCl buffer (pH 8.5) | 0.5 ml |
| 0.6 mM | NAD(P)H | 0.5 ml |

Procedure

The reaction solution (1.0 ml) of the above composition is taken in a 2.0 ml quarz cell and incubated at 37° C. for 5 minutes. To the resultant solution is added under stirring 0.2 ml of the G6PDH solution of its concentration adjusted at 5000 U/ml and then, the reduction of $A_{340}(\Delta A)$ is periodically measured at 37° C. The activity of NAD(P)H oxidase which decreases NAD(P)H at a rate of 1 μmol/min, is defined as 1 unit (U).

$$U/ml = \frac{\Delta A}{T} \times \frac{1}{6.22} \times \frac{1.2}{0.2}$$

T; Reaction time
6.22; millimolar extinction coefficient of NAD(P)H at 340 nm (cm²/μmol)

(3) Assay of lactate dehydrogenase activity

| Reaction solution | | |
|---|---|---|
| 0.2M | Tris-HCl buffer (pH 8.5) | 0.2 ml |
| 0.1M | Sodium pyruvate | 0.1 ml |
| 3 mM | NAD(P)H | 0.1 ml |
| | Distilled water | 0.6 ml |

Procedure

The reaction solution (1.0 ml) of the above composition is taken in a 2.0 ml quarz cell and incubated at 37° C. for 5 minutes. To the resultant solution is added under stirring 0.2 ml of the G6PDH solution of its concentration adjusted at 5000 U/ml and then, the reduction of $A_{340}(\Delta A)$ is periodically measured at 37° C. The activity of lactate dehydrogenase which decreases NAD(P)H at a rate of 1 μmol/min, is defined as 1 unit (U).

$$U/ml = \frac{\Delta A}{T} \times \frac{1}{6.22} \times \frac{1.2}{0.2}$$

T; Reaction time
6.22; millimolar extinction coefficient of NAD(P)H at 340 nm (cm²/μmol)

(2) Physico-chemical properties (a) Enzymatic action: Catalyze the enzymatic reaction to produce gluconolactone-6-phosphate and NAD(P)H from glucose-6-phosphate and NAD(P).

(b) Substrate specificity; Acts at least with glucose-6-phosphate.

| Substrate | Relative activity (%) |
|---|---|
| Glucose-6-phosphate | 100 |
| Mannose-6-phosphate | 38.5 |
| Galactose-6-phosphate | 19.3 |
| Fructose-6-phosphate | 0 |
| Glucose-1-phosphate | 0 |
| Glucosamine-6-phosphate | 0 |

-continued

| Substrate | Relative activity (%) |
|---|---|
| 6-Phosphogluconic acid | 0 |
| Coenzyme | Km value (mM) |
| NADP | about $8.3 \times 10^{-3}$ |
| NAD | about 1.2 |

(c) Optimum pH; 8 to 9

Buffer solutions having different pHs are used to measure an optimum pH according to the aforementioned enzyme assay method. The results show that the optimum pH is in a range of 8 to 9.

(d) Isoelectric point; 6.1±0.6

Isoelectric-point electrophoresis using AMPHOLINE PAGPLATE® manufactured by LKB CO. LTD. is used to determine its isoelectric point. The results show that the isoelectric point is pI 6.1 ±0.6.

(e) Thermal stability; stable against a treatment at about 65° C. for 15 minutes.

When a sample of G6PDH is treated in 40 mM Tris-HCl buffer of pH 7.5 at various temperatures for 15 minutes, there remains the activity of about 100% at 65° C. or less and about 70% at 70° C.

(f) pH Stability; stable at pH 6 to 8 (at 70° C. for 15 minutes).

As for pH testing buffers, 40 mM DMG (dimethyl-glutaric acid) buffer is used in a pH range of 4.5 to 6.5; 40 mM phosphate buffer, in a pH range of 6.0 to 8.0; 40 mM Tris-HCl buffer, in a range of 7.0 to 9.0.

(g) Molecular weight; about 270,000.

Molecular weight is determined by column chromatography on TSK-Gel G3000 SW. The following proteins are used as reference proteins;

| Ovalbumin | 45,000 |
|---|---|
| Bovine serum albumin | 67,000 |
| Aldorase (from rabbit muscle) | 150,000 |
| Catalase (calf liver) | 210,000. |

The molecular weight measured is comparatively studied with the amino acid sequence of G6PDH and the present G6PDH is estimated to exist in the form of an associated body of the polypeptides of 4 to 6.

(h) Inhibitor; Activity is inhibited by the presence of $Mn^{2+}$, $Cu^{2+}$, $Al^{3+}$.

In the present specification, the following abbreviations referring to amino acid, peptide, nucleic acid, and others are used, which comply with abbreviations commonly used in the art. All amino acids represent L-form thereof.

| DNA: | deoxyribonucleic acid |
|---|---|
| RNA: | ribonucleic acid |
| A: | adenine |
| T: | thymine |
| G: | guanine |
| C: | cytosine |
| Ala: | alanine |
| Arg: | arginine |
| Asn: | asparagine |
| Asp: | aspartic acid |
| Cys: | cysteine |
| Gln: | glutamine |
| Glu: | glutamic acid |
| Gly: | glycine |
| His: | histidine |
| Ile: | isoleucine |

-continued

| Leu: | leucine |
| Lys: | lysine |
| Met: | methionine |
| Phe: | phenylalanine |
| Pro: | proline |
| Ser: | serine |
| Thr: | threonine |
| Trp: | tryptophan |
| Tyr: | tyrosine |
| Val: | valine |

Examples are given below to further illustrate the present invention. The present invention is not limited to these examples.

EXAMPLE 1

Isolation of chromosomal DNA

Chromosomal DNA was isolated by the following method from the *Bacillus* sp. HT-3 strain defined as FERM BP-2172. The bacterial strain was cultured with shaking in 150 ml of the normal bouillon medium at 50° C. overnight, centrifuged at 3000 rpm for 10 minutes and harvested. To the harvested cells was added 10 mg/ml lysozyme solution in 5 ml of the solution containing 10% saccharose, 50 mM Tris-HCl buffer (pH 8.0) and 50 mM EDTA and kept at 37° C. for 15 minutes followed by adding 1 ml of 10% SDS (sodium dodecylsulfate) solution. To the resultant suspension was added an equal volume of a mixed solution of chloroform and phenol (1:1) and mixed under agitation followed by centrifugation at 10000 rpm for 3 minutes in order to separate an aqueous phase from a solvent phase. On the separated aqueous phase was layered two-fold volume of ethanol and DNA was isolated in a form of being wound round a glass rod while gradually being stirred with the glass rod. The DNA isolated was dissolved in 10 ml of the solution containing 10 mM Tris-HCl buffer (pH 8.0) and 1 mM EDTA (this solution is abbreviated as TE hereinafter), to treat with an identical volume of a mixed solution of chloroform-phenol (1:1) and centrifuged to separate an aqueous phase. Subsequently two-fold volume of ethanol was added to the separated aqueous phase and the same procedure described above was conducted to isolate DNA again, which was solubilized in 2 ml of TE.

EXAMPLE 2

Isolation of pACYC184 plasmid DNA

*Escherichia coli* pM191possessing pACYC184 (see J. Bacteriol. 134, 1441(981); ATCC 37033) was cultured with shaking in 1 l of the BHI medium (product of Difco Laboratories). When the turbidity of the medium reached $OD_{660}=1.0$, spectinomycin was added thereto to a final concentration of 300 μg/ml and further shaked at 37° C. over 16 hours. The bacterial cells were collected by centrifugation at 3000 rpm for 10 minutes, which were treated for preparation of the plasmid DNA with the lysozyme-SDS and cesium chloride-ethidium bromide methods disclosed by Maniatis in Molecular Cloning, pp. 86–94, Cold Spring Harbor (1982).

EXAMPLE 3

Construction of plasmid pG6PDH 1 having G6PDH gene (i) The chromosomal DNA (2 μl; about 0.5 g) of the *Bacillus* sp. HT-3 strain prepared in Example 1, was mixed with 1 μl of a cleaving buffer of ten-fold concentration as much as that when an enzymatic reaction was effected [100 mM Tris-HCl (pH 8.0), 70 mM $MgCl_2$, 1.0 M KCl, 70mM mercaptoethanol], 1 μl of 3 units/ml MboI (manufactured by Takara, Co.) and 6 μl of water and cleaved at 37° C. for 1 hour. Plasmid pACYC184 DNA (about 0.3 g) prepared alternatively was cleaved with BamHI following the same technique, and then 0.6 unit of alkaline phosphatase was further added thereto to incubate at 65° C. for 1 hour. The two solutions containing each cleaved DNA were mixed together, to which was added one-tenth volume of 3 M sodium acetate. The resulting solution was treated with the chloroform-phenol mixture solution of a volume identical to the total volume of the resulting solution and centrifuged to separate an aqueous phase, to which was added two-fold volume of ethanol and centrifuged to precipitate DNA. The DNA was dried under reduced pressure and dissolved in 89 μl of water followed by adding and mixing 10 μl of a ligation-buffer of ten-fold concentration composed of 0.5 M Tris-HCl (pH 7.6), 0.1 M $MgCl_2$, 1.0 M dithiothreithol, 10 mM spermidine and 10 mM ATP together with 1 μl (175 units) of T4 DNA ligase (manufactured by Takara, Co.). The resulting DNA solution was kept to stand at 4° C. overnight. The DNA solution was treated with chloroform and phenol, and an ethanol-precipitate was separated, dried under reduced pressure and dissolved again in 10 μl of TE.

(ii) The *Escherichia coli* DH1 strain in the logarithmic growth phase, cultured in 100 ml of the BHI medium (the strain was supplied by the National Institutes of Genetics in Japan; its stock number was ME8569; ATCC 33849) was collected by centrifugation at 10000 rpm for 2 minutes and suspended into 40 ml of the ice-cold solution containing 30 mM potassium acetate (pH 5.8), 100 mM RbCl, 10 mM $CaCl_2$, 50 mM $MnCl_2$ and 15% glycerin. After being kept at 0° C. for 5 minutes, the solution was centrifuged to discard the supernatant. The collected precipitate was again suspended into 4 ml of the solution containing 10 mM MOPS buffer (manufactured by Dohtite Co.) (pH 6.5), 75 mM $CaCl_2$, 10 mM RbCl and 15% glycerin and kept to stand at 0° C. for 15 minutes. The resultant cells were used as competent cells.

(iii) To 200 μl of the suspension of cells was added 10 μl of the DNA solution prepared in (i) and kept to stand at 0° C. for 30 minutes, followed by addition of 1 ml of the BHI medium. The resultant solution of 100 μl was spread on a BHI agar plate containing 25 μg/ml chloramphenicol and cultured at 37° C. overnight to produce transformants. The transformants were replicated on a plate of assaying agar (it is composed of 4 ml of 1 M phosphate buffer (pH 6.5), 1 ml of 10% Triton X-100, 1 ml of 100 mM NADP, 1 ml of 500 U/ml diaphorase, 2.5 ml of 1% NBT, 2 ml of 1 M glucose-6-phosphate, 1.5 g of agar and 88.5 ml of distilled water), and subjected to the observation of its color change at room temperature.

The transformant formed colonies of about 4500 in number. It was found that one colony among about 4500 transformants changed in blue more intensively than other colonies and this bacterial strain was defined as *Escherichia coli* DH1 . pG6PDH1strain, FERM 2174. After isolation and purification, the bacterium was cultured in the BHI medium at 37° C. overnight to examine its G6PDH production potential, which was found to be 18 U/ml as the G6PDH activity.

The plasmid possessed by the bacterial strain was isolated according to the procedure in Example 2, which was defined as pG6PDH1 containing the G6PDH gene and the pACYC 184 gene.

EXAMPLE 4 pG6PDH1 Mapping and Determination of the nucleotide sequence of G6PDH gene.

pG6PDH1 Plasmid DNA was prepared from *Escherichia coli* DH1 . pG6PDH1 strain according to the same procedure for pACYC 184.

The cleavage map of pG6PDH1 plasmid DNA with restriction enzymes, EcoRI, ClaI, EcoRV, HindIII, BglII, BamHI, SphI, NruI, HpaI, MluI, NcoI, ApaLI and XbaI (the restriction enzymes all were products by Takara, Co.) was prepared. The results were shown in FIG. 3. The nucleotide sequence of the DNA containing the G6PDH gene was determined by the di-deoxy method using M13 phage [Science 214, 1205–1210 (1981)]. The amino acid sequence and nucleotide sequence of the G6PDH structural gene were shown in FIGS. 1 and 2, respectively.

EXAMPLE 5

G6PDH Production

*Escherichia coli* DH1.pG6PDH1 strain was cultured in 4 l of the BHI medium (Difco Laboratories) containing 30 μg/ml chloramphenicol (Sankyo Pharmaceuticals, Co.) in a jar-fermentator at 37° C. for 18 hours and harvested by centrifugation at 5000 rpm for 15 minutes.

The harvested bacteria were washed with 1 l of 20 mM phosphate buffer (pH 7.0) and suspended in 500 ml of 20 mM phosphate buffer (pH 7.0). To the resultant suspension were added lysozyme, EDTA-2Na and Triton X-100 to final concentrations being 1 mg/ml, 2 mM and 0.1%, respectively, and then, kept to stand at 37° C. for 30 minutes followed by pH adjustment to 7.0, which was treated with heating at 60° C. for 6 hours and centrifuged at 5000 rpm for 15 minutes to separate 420 ml of the supernatant (the activity of G6PDH was 162 U/ml). To the supernatant was added 840 ml of acetone followed by centrifuging at 5000 rpm for 15 minutes to separate the precipitate, which was resuspended in 500 ml of 20 mM phosphate buffer (pH 7.0) and centrifuged at 5000 rpm for 15 minutes, resulting in the separation of 480 ml of the supernatant (the activity of G6PDH was 114 U/ml). Ion-exchange chromatography on a DEAE-Sepharose CL-6B (Pharmacia Fine Chemicals, Co.) column bufferized with 20 mM phosphate buffer (pH 7.0) was conducted to fractionate active fractions, which were pooled and desalted using a seamless cellulose tubing to yield an enzyme product of 300 ml. Its G6PDH activity was 148 U/ml.

Comparative example 1

Conventional example

*Bacillus sp* HT-3 (FERM BP-2172) was cultured in 4 l of the BHI medium (Difco Laboratories) in a jar-fermentator at 55° C. for 18 hours and harvested by centrifugation at 5000 rpm for 15 minutes.

The harvested bacteria were washed with 1 l of 20 mM phosphate buffer (pH 7.0) and suspended in 500 ml of 20 mM phosphate buffer (pH 7.0). To the resultant suspension were added lysozyme, EDTA-2Na and Triton X-100 to final concentrations of being 1 mg/ml, 2 mM and 0.1%, respectively, and then, kept to stand at 37° C. for 30 minutes followed by pH adjustment to 7.0, which was treated with heating at 60° C. for 6 hours and centrifuged at 5000 rpm for 15 minutes to separate 420 ml of the supernatant. To the supernatant was added 840 ml of acetone followed by centrifugation at 5000 rpm for 15 minutes to separate the precipitate, which was resuspended in 500 ml of 20 mM phosphate buffer (pH 7.0) and centrifuged at 5000 rpm for 15 minutes, leading to the separation of 480 ml of the supernatant. Ion-exchange chromatography on a DEAE-Sepharose CL-6B (Pharmacia Fine Chemicals, Co.) column bufferized with 20 mM phosphate buffer (pH 7.0) was conducted to fractionate active fractions, which were pooled and desalted using a seamless cellulose tubing. Chromatography on an octyl-Sepharose CL-4B (Pharmacia Fine Chemicals, Co.) column bufferized with 30% saturated ammonium sulfate was conducted to fractionate active fractions, which were pooled and desalted using a seamless cellulose tubing. Chromatography on hydroxylapatite (KOKEN, Co.) was subsequently conducted to fractionate active fractions, which were pooled and desalted using a seamless cellulose tubing. Chromatography on a blue-Sepharose (Pharmacia Fine Chemicals, Co.) column was conducted to fractionate active fractions, which were pooled and desalted using a seamless cellulose tubing to yield an enzyme product.

A small amount of BSA of RIA grade (Sigma Co.) was added to each enzyme product of Example 5 and Comparative Example 1, and lyophilized according to the conventional method. Specific activity each of G6PDH, NAD(P)H oxidase (NAD(P)Hox) and lactate dehydrogenase (LDH) in lyophilized products was measured as shown in the following results.

|  | G6PDH (U/mg) | NAD(P)Hox (U/mg) | LDH (U/mg) |
|---|---|---|---|
| Example 5 | 103.1 | —* | —* |
| Comparative example | 87.3 | 0.026 | 0.017 |

*—: 0.0001 U or less per 100 U of G6PDH

According to the present invention, DNA coding the amino acid sequence shown in FIG. 1 or DNA shown in FIG. 2 and the transformant possessing the DNA are used for the process for producing G6PDH in a large scale with stability by culturing the transformant. G6PDH having a surprisingly excellent long-term stability and thermal stability is obtained without contaminating enzymes causing diagnostic problems.

We claim:

1. A process for preparing glucose-6-phosphate dehydrogenase, comprising
   culturing a transformant transformed by a plasmid comprising exogenous DNA which encodes the amino acid sequence shown from its N-terminal in FIG. 1 in order to express said DNA, and
   harvesting glucose-6-phosphate dehydrogenase from the resulting culture.

2. A process for preparing glucose-6-phosphate dehydrogenase, comprising
   culturing a transformant transformed with a plasmid comprising DNA shown from its 5'-terminal in FIG. 2 in order to express said DNA, and
   harvesting glucose-6-phosphate dehydrogenase from the resulting culture.

3. The process for preparing glucose-6-phosphate dehydrogenase according to claim 1, wherein the activity of each NAD(P)H oxidase and lactase dehydrogenase as contaminating enzymes in the collected glucose-6-phosphate dehydrogenase is 0.0001 unit or less in 100 units of glucose-6-phosphate dehydrogenase activity and the glucose-6-phosphate dehydrogenase has at least the following physico-chemical properties:
  (a) catalyzes an enzymatic reaction to produce gluconolactone-6-phosphate and NAD(P)H from glucose-6-phosphate and NAD(P);
  (b) has an optimum pH within the range of 8 to 9;
  (c) has an isoelectric point of 6.1 ±0.6;
  (d) is thermally stable after treatment at about 65° C. for 15 minutes; and
  (e) is stable within the range of pH 6 to 8 at 70° C. for 15 minutes.

4. An isolated DNA encoding the amino acid sequence shown from its N-terminal in FIG. 1.

5. An isolated DNA according to claim 4, wherein the nucleotide sequence of the DNA is shown from its 5'-terminal in FIG. 2.

6. A plasmid comprising DNA encoding the amino acid sequence shown from its N-terminal in FIG. 1.

7. A transformant transformed by a plasmid comprising DNA which encodes the amino acid sequence shown from its N-terminal in FIG. 1, said DNA being heterologous to said transformant before its transformation.

8. The transformant according to claim 7 wherein the transformant is a bacterium of the genus and species *Escherichia coli.*

9. The transformant according to claim 8, wherein the transformant is *Escherichia coli* DH1.pG6PDH deposited as FERM BP-2174 at the Agency of Industrial Science and Technology, the Fermentation Research Institute.

* * * * *